United States Patent [19]

Bolund et al.

[11] Patent Number: 5,164,394
[45] Date of Patent: * Nov. 17, 1992

[54] METHOD FOR TREATING HYPERPROLIFERATIVE SKIN DISEASES

[75] Inventors: Lars Bolund, Risskov; Peter K. A. Jensen, Ry; Peter Bjerring, Risskov, all of Denmark

[73] Assignee: Senetek, PLC, St. Louis, Mo.

[ * ] Notice: The portion of the term of this patent subsequent to Jun. 4, 2008 has been disclaimed.

[21] Appl. No.: 679,732

[22] Filed: Apr. 3, 1991

Related U.S. Application Data

[63] Continuation of Ser. No. 364,364, Jun. 8, 1989, Pat. No. 5,021,422.

[51] Int. Cl.$^5$ ............................................. A61K 31/52
[52] U.S. Cl. .................................. 514/261; 514/266; 514/861; 514/864
[58] Field of Search ............... 514/261, 266, 861, 864

[56] References Cited

U.S. PATENT DOCUMENTS 5,021,422  6/1991  Bolund et al. ...................... 514/261

FOREIGN PATENT DOCUMENTS 0103878  3/1984  European Pat. Off. .
6019709  1/1985  Japan .

OTHER PUBLICATIONS

Chemical Abstracts 74:57212c (1971).
Orr and McSwain, The Effects of Kinetin Upon Epithelium and Fibroblasts in Tissue Culture, Cancer 10, 617–624 (1957).
Johnson, et al., N$^6$-Substituted Adenines Induce Cell Elongation Irrespective of the Intracellular Cyclic AMP Levels, Exptl. Cell. Res. 85, 47–56 (1974).
Hecht et al. Competitive Inhibition of Beef Heart Cyclic AMP Phosphodiesterase by Cytokinins and Related Compounds, Proc. Natl. Acad. Sci. (U.S.A.) 71, 4670–4674 (1974).
Mookerjee et al., Effects of Plant Cytokinins on Human Lymphocyte Transformation, J. Reticuloendoth. Soc. 25, 299–314 (1979).
Gordon and Seglen, 6-Substituted Purines: A Novel Class of Inhibitors of Endogenous Protein Degradation in Isolated Rat Hepatocytes, ARc. Biochem. Biophys. 217, 282–294 (1982).
Vesely et al., Plant Growth-Promoting Hormones Activate Mammalian Guanylate Cyclase Activity, Endocrinology 116, 1887–1892 (1985).

Primary Examiner—Leonard Schenkman
Attorney, Agent, or Firm—Fitch, Even, Tabin & Flannery

[57] ABSTRACT

It has been discovered that 6-(substituted amino)purine cytokinins, such as kinetin, induce differentiation, and consequently reduce or eliminate the abnormally high rate of proliferation, of hyperproliferating cells associated with hyperproliferative skin diseases. Thus, the present invention provides methods and compositions for treating hyperproliferative skin diseases in mammals, particularly such diseases associated with hyperproliferating epidermal cells in humans, by administering to the hyperproliferating cells associated with such a disease, in the skin of a mammal suffering therefrom, a differentiation-inducing effective amount of a 6-(substituted amino)purine cytokinin.

6 Claims, No Drawings

METHOD FOR TREATING HYPERPROLIFERATIVE SKIN DISEASES87

This is a continuation of application Ser. No. 364,364, filed Jun. 8, 1989 now U.S. Pat. No. 5,021,422.

TECHNICAL FIELD

The present invention concerns methods and compositions for treating diseases associated with hyperproliferating epidermal cells, particularly disorders of skin in humans.

BACKGROUND OF THE INVENTION

Among diseases afflicting mammals, and particularly humans, are many which are due to hyperproliferation of epidermal cells. Among such diseases are skin diseases such as basal cell carcinoma, malignant melanoma, squamous cell carcinoma, actinic keratosis, Bowen's Disease, papilloma, seborrheic kera- tosis, toxic eczema, allergic eczema, atopic dermatitis, ichthyosis, and psoriasis.

The present invention provides methods and compositions for treating such hyperproliferative skin diseases.

The methods and compositions of the invention involve cytokinins. Cytokinins are plant hormones involved in promoting growth and cell division in explants of plant tissue in culture in standard media, which contain auxins (another class of plant hormones) as well as vitamins, mineral salts, and sugar.

Among cytokinins are those which are 6-(substituted amino)purines, including kinetin (6-(furfuryl)aminopurine), zeatin (6-(3-hydroxymethyl, 3-methylallyl)aminopurine, 6-(3,3-dimethylallyl)aminopurine, 6-(benzyl)aminopurine, 6-(phenyl)aminopurine, 6-(n-alkyl)aminopurine, wherein the alkyl group has 4, 5 or.6 carbon atoms, and 6-(cyclohexyl)methylaminopurine.

Cytokinins have been observed to have various effects on mammalian cells in culture. Orr and McSwain, Cancer 10, 617-624 (1957); Johnson et al., Exptl. Cell Res. 85, 47-56 (1974); Hecht et al., Proc. Natl. Acad. Sci. (USA) 71, 4670-4674 (1974); Mookerjee et al., J. Reticuloendoth. Soc. 25, 299-314 (1979); Gordon and Seglen, Arch. Biochem. Biophys. 217, 282-294 (1982); Vesely et al., Endocrinology 116, 1887-1892 (1985).

SUMMARY OF THE INVENTION

It has been found unexpectedly that hyperproliferating epidermal cells associated with hyperproliferative skin diseases of mammals, when exposed to 6-(substituted amino)purine cytokinins, are caused to differentiate and slow in their rate of proliferation.

Thus, the present invention entails methods and compositions for treating hyperproliferative skin diseases of mammals, including humans. According to the methods of the invention, differentiation-inducing-effective amounts of a 6-(substituted amino)purine are administered to the hyperproliferating epidermal cells associated with such a disease in a mammal suffering therefrom.

DETAILED DESCRIPTION OF THE INVENTION

In one of its aspects, the present invention entails a method of treating an hyperproliferative skin disease in a mammal suffering therefrom which method comprises administering to the hyperproliferating cells, associated with said disease, of the skin of said mammal a differentiation-inducing effective amount of a 6-(substituted amino)purine cytokinin.

In another of its aspects, the invention entails a composition for treating an hyperproliferative skin disease of a mammal, which composition comprises a 6-(substituted amino)purine cytokinin and a physiologically acceptable vehicle for application of said cytokinin to the outer surface of the skin of a mammal suffering from said disease such that said cytokinin is brought into contact with (i.e., administered to) the hyperproliferating cells associated with the disease.

The present invention is preferably employed to treat hyperproliferative skin diseases of humans.

Such diseases, in humans and other mammals, are due to hyperproliferating epidermal cells of the skin. Among such diseases, that can be treated in accordance with the present invention, are basal cell carcinoma, malignant melanoma, squamous cell carcinoma, actinic keratosis, Bowen's Disease, papilloma, seborrheic keratosis, toxic eczema, allergic eczema, atopic dermatitis, ichthyosis, and psoriasis.

In accordance with the method of the invention, a 6-(substituted amino)purine cytokinin is brought into contact with (i.e., administered to) the hyperproliferating cells associated with an hyperproliferating skin disease in an amount which is effective to induce such cells to differentiate.

Among the 6-(substituted amino)purine cytokinins which can be employed in accordance with the invention are those of formula I:

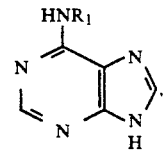

wherein $R_1$ is selected from the group consisting of furfuryl, phenyl, benzyl, n-alkyl of 4, 5 or 6 carbon atoms, (cyclohexyl)methyl ($-CH_2(C_6H_{11})$), (3-hydroxymethyl-3-methyl)allyl

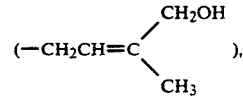

and 3,3-dimethylallyl ($-CH_2CH=C(CH_3)_2$) Most preferred among these is kinetin ($R_1$ being furfuryl).

For carrying out the method of the invention, the 6-(substituted amino)purine cytokinin is combined, at a concentration of between about 0.01% (w/v) and about 0.5% (w/v), preferably about 0.1% (w/v) with physiologically acceptable vehicle, such as a standard, commonly used skin-moisturizing vehicle. One example of the many such skin-moisturizing vehicles is a composition of 4–8 wt. % (e.g., 6.2 wt. %) glycerol mohostearate 40–50, 12–16 wt. % (eg., 14.3 wt. %) white petroleum, 0.5–2 wt. % (e.g., 1 wt. %) lanolin, 9–13 wt. % (e.g., 11.4 wt. %) mineral oil, 0.5–2 wt. % (e.g., 1 wt. %) propylene glycol, 1–2 wt. % (e.g., 1.4 wt. %) triethanolamine (bp-80), 1–5 wt. % (e.g., 3.3 wt. %) stearin, 0.5–2 wt. % (e.g., 1 wt. %) parahydroxybenzoic acid, and the remainder (e.g., 60.4 wt. %) water. Alternatively, the 6-(substituted amino)purine cytokinin can be combined with a lipogel-type vehicle, such as that being sold by Rhone-Poulenc (Courbevoie, France) under the tradename CERIDAL ™, at a concentration of between about 1 and about 5 mg/ml. The resulting composition according to the invention is applied topically to the surface of the area of the skin affected by the hyperproliferative disease (i.e., the area under, or as a part of, which the hyperproliferating epidermal cells associated with the disease are located), usually with light rubbing or message or the like as commonly employed in the application of moisturizing vehicles or lipogel-based compositions.

It is contemplated that the method of the invention will be carried out under the guidance of a dermatologist or other physician or, in the case of a non-human mammal, veterinarian.

The frequency of application most suitable for treating a particular disease in a particular mammal with a particular composition according to the invention will be readily determined by the skilled and will depend, as the skilled will understand, on numerous factors, such as the species of mammal, the nature of the disease, the severity of the disease, the moisturizing vehicle, lipogel-based vehicle or other physiologically acceptable vehicle employed in the composition, and the concentration of the 6-(substituted amino)purine cytokinin in the composition. Generally, application of a composition according to the invention to an affected area of the skin between once and four times daily (preferably twice) for between about a week and about a year, more typically about a month, will be effective to induce hyperproliferating cells under, or in, the area to differentiate to a non-proliferating or normally proliferating state and thereby substantially cure the hyperproliferative disease of the affected area.

The invention will now be illustrated in the following Example.

EXAMPLE

Primary explant cultures of human epidermal cells from psoriatic skin of two persons suffering from psoriasis were established by taking skin samples, cutting the sample into small (approx. 2×2 mm$^2$) pieces, and explanting the pieces into ordinary tissue culture flasks, where culture growth was carried out at 35° C. with a standard keratinocyte culture medium (Dulbecco's Modified Eagle's Medium+20% fetal calf serum+10 ng/ml epidermal growth factor+0.4 µg/ml hydrocortisone).

Cultures were stripped by a standard procedure after growth for one month. That is, they were incubated for 72 hours in low Ca$^{++}$ medium prior to selectively stripping off all the supra basal layers. After the stripping, the cultures were re-fed with medium with normal Ca$^{++}$ concentration In half of the cultures from each patient, kinetin was present in the culture medium at 200 µM concentration.

The morphology of cells in the primary, unstripped cultures was examined after one month plus ten days of growth. In the cultures fed with kinetin, in comparison with those not so fed, there was a large decrease in mitotic figures and some indication of increased differentiation (accumulation of numerous, filament-containing cells in discrete, elevated areas).

The morphology of cells in the stripped cultures was also examined, after seven days of growth after the stripping. In the cultures fed with kinetin, in comparison with those not so fed, there was much more heterogeneity in morphology. In the cultures fed with kinetin, in comparison with those not so fed, there was a reduction of mitotic figures, reduction of multilayering, no lateral growth, early in the observation period a vacuolization of the cytoplasm in many cells, late in the observation period areas with numerous cornified envelope-containing cells alternating with empty looking areas.

At seven days post-stripping, cultures were labeled using $^3$H-labeled thymidine for 30 minutes. S-phase cells were sorted out onto glass slides, on the basis of EtBr-Mithramycin staining using a FACS-II cell sorter, and then subjected to autoradiography. The numbers of labeled and unlabeled S-phase cells, and the number of grains per nucleus in the labeled cells, were then measured microscopically. In cultures with kinetin, more than 70% of S-phase cells were unlabeled (i.e., 0–3 grains per nucleus) and about 5% of S-phase cells were highly labeled (>25 grains per nucleus). In cultures without kinetin, about 30% of S-phase cells were unlabeled and about 40% of S-phase cells were highly labeled. These results indicate that kinetin inhibited the regenerative response in psoriatic cells.

The cornified envelope formed by cultured keratinocytes is regarded as a marker of differentiation. The fraction of cells in a culture that has acquired a cornified envelope can be measured by a standard method, wherein the cells in the culture are counted, then treated with SDS and reducing agents, which destroys cells without the envelope but to which the envelope is resistant, and then recounted. With cultures of psoriatic cells from one of the persons suffering from psoriasis, in which cells with cornified envelope were determined 7-days post-stripping, 37% of the cells in cultures treated with kinetin had a cornified envelope while 18% of the cells in cultures not treated with kinetin had a cornified envelope. With cultures of psoriatic cells from the other of the persons suffering from psoriasis, in which cells with cornified envelope were determined 7-days post-stripping, 14% of the cells in cultures treated with kinetin had a cornified envelope while 12% of the cells in cultures not treated with kinetin had a cornified envelope. These results indicate that kinetin stimulated differentiation of the psoriatic cells.

While the invention has been described with some specificity in the instant specification, persons of skill in the art will recognize modifications and variations of what has been described that fall within the spirit of the invention. It is intended that such modifications and variations be encompassed by the following claims.

What is claimed is:

1. A method of treating an hyperproliferative skin disease in an human suffering therefrom which method comprises administering to the hyperproliferating cells, associated with said disease, of the skin of said human a differentiation-inducing-effective amount of a 6-(substituted amino)purine cytokinin.

2. A method according to claim 1, wherein the disease is selected from the group consisting of actinic keratosis, Bowen's Disease, papilloma, seborrheic keratosis, toxic eczema, allergic eczema, atopic dermatitis, ichthyosis.

3. A method according to claim 1, wherein the 6-(substituted amino)purine cytokinin is of formula I:

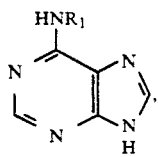

wherein R₁ is selected from the group consisting of furfuryl, phenyl, benzyl, n-alkyl of 4, 5 or 6 carbon atoms, (cyclohexyl)methyl, (3-hydroxymethyl-3-methyl)allyl, and 3,3-dimethylallyl.

4. A method according to claim 3 wherein the 6-(substitued amino)purine cytokinin is kinetin.

5. A method according to claim 2, wherein the 6-(substituted amino)purine cytokinin is of formula I:

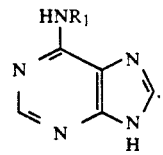

wherein R₁ is selected from the group consisting of furfuryl, phenyl, benzyl, n-alkyl of 4, 5 or 6 carbon atoms, (cyclohexyl)methyl, (3-hydroxymethyl-3-methyl)allyl, and 3,3-dimethylallyl.

6. A method according to claim 5 wherein the 6-(substituted amino)purine cytokinin is kinetin.

* * * * *

UNITED STATES PATENT AND TRADEMARK OFFICE
CERTIFICATE OF CORRECTION

PATENT NO. : 5,164,394
DATED : November 17, 1992
INVENTOR(S) : Bolund, et. al.

It is certified that error appears in the above-indentified patent and that said Letters Patent is hereby corrected as shown below:

On the Title page, item [56] other Publications, under the "Gordon" reference, change "ARc." to --Arch.--.

Column 1, line 2, after "DISEASES" delete "87".

Column 2, line 50, after "$(-CH_2CH=C(CH_3)_2)$" insert a period (.).

Column 2, line 60, change "(eg.," to --(e.g.,--.

Signed and Sealed this

Twenty-first Day of December, 1993

Attest:

BRUCE LEHMAN

*Attesting Officer*     *Commissioner of Patents and Trademarks*